United States Patent [19]

Sasaki et al.

[11] 4,436,657

[45] Mar. 13, 1984

[54] ANTITUMOR GLYCOPROTEIN SUBSTANCE AND PREPARATION THEREOF

[75] Inventors: Takuma Sasaki, Tokyo; Kazuya Nakamichi; Yakudo Tachibana, both of Sohka; Kiyoshi Minami, Koshigaya, all of Japan

[73] Assignee: Maruzen Oil Co., Ltd., Osaka, Japan

[21] Appl. No.: 519,725

[22] Filed: Aug. 2, 1983

[30] Foreign Application Priority Data

Aug. 9, 1982 [JP] Japan .................................. 57-137210

[51] Int. Cl.³ ............................ A23J 1/04; C07G 7/00
[52] U.S. Cl. .................................. 260/112 R; 424/95; 424/177
[58] Field of Search .................................... 260/112 R

[56] References Cited

U.S. PATENT DOCUMENTS

| 3,862,122 | 1/1975 | Peniston et al. | ............ 260/112 R X |
| 4,199,496 | 4/1980 | Peniston et al. | ................ 260/112 R |
| 4,390,468 | 6/1983 | Sasaki et al. | ..................... 260/112 R |

OTHER PUBLICATIONS

J. of National Cancer Institute, vol. 60, No. 6, pp. 1499-1500, Jun. 1978, Sasaki et al.

*Primary Examiner*—Howard E. Schain
*Attorney, Agent, or Firm*—Larson and Taylor

[57] ABSTRACT

A novel glycoprotein substance possessing a high antitumor activity is provided, which is recovered and isolated from the liquid portion coming from cooking of raw scallop with a hot aqueous solvent or vapor of such solvent and which is amphoteric electrolyte in nature with an average molecular weight of about 470,000 and with an isoelectric point of pH 5.5.

6 Claims, 3 Drawing Figures

FIG. 1

FIG. 3

ANTITUMOR GLYCOPROTEIN SUBSTANCE AND PREPARATION THEREOF

FIELD OF THE INVENTION

This invention relates to a novel antitumor glycoprotein substance and a process for the preparation thereof from scallop.

BACKGROUND OF THE INVENTION

We have already found and reported that several antitumor substances are obtained from meat portion of shellfish and exhibit wide antitumor spectra with little or no cytotoxicity (refer to Japanese Patent Publication No. 8088/82 and Japanese Patent KOKAI Nos. 41314/79 and 41315/79). To be concrete, the first substance we found is a water-soluble, thermally stable glycoprotein having a molecular weight range within the limits of 100,000 and 300,000 (Japanese Patent Publication No. 8088/82). Japanese Patent KOKAI No. 41314/79 describes four substances all of which are water-soluble glycoprotein substances having an average molecular weight of about 20,000 and an isoelectric point of pH 4.5 with somewhat different physical properties from one another and are extracted from meat portion of scallop from which the liver has been removed. Japanese Patent KOKAI No. 41315/79 provides a water-soluble glycoprotein substance having an average molecular weight of 10,000~30,000 which is obtained from meat portion of shellfish, particularly of scallop, wreath shell, tokobushi (Haliotis japonica) and pearl-oyster, from which the liver has been removed.

After that, we have further found that the liquid portion which comes from cooking of raw shellfish with a hot aqueous solvent or with the vapor of such solvent for taking up edible portions thereof and which is to be discarded as waste can also serve as raw material from which watersoluble, macromolecular glycoprotein substances similar to those already obtained from shellfish as above-mentioned are recovered and that these substances have a range of molecular weights within the limits of from 10,000 to 300,000 and possess a significant antitumor activity (refer to T. Sasaki et al, U.S. patent application Ser. No. 404,971, now U.S. Pat. No. 4,390,468).

Thus, the known antitumor substances derived from shellfish may be divided into two broad classes, namely water-soluble glycoproteins having a molecular weight range within the limits of 10,000 and 30,000, typically of around 20,000, and those having a molecular weight range within the limits of 100,000 and 300,000.

We have continued our investigations on antitumor substances derived from scallop, particularly from the liquid waste portion coming from cooking of raw scallop and now found the presence in the dry powder recovered from said waste liquid of new antitumor substance having much higher average molecular weight than those of all the known antitumor glycoprotein substances derived from shellfish. On the basis of this discovery, we have followed up our study thereon and successfully isolated a new antitumor glycoprotein substance and determined physico-chemical properties and antitumor activities thereof.

SUMMARY OF THE INVENTION

Accordingly, it is the main object of this invention to provide a novel glycoprotein substance possessing a significant antitumor activity. Another object of this invention is to provide a process for the preparation of the novel glycoprotein substance from the liquid portion, i.e. waste liquor, coming from cooking of raw scallop. A further object of this invention is to provide an antitumor agent with a low toxicity. These and other objects of this invention will become clear from the following descriptions.

According to the first aspect of this invention, therefore, there is provided a glycoprotein substance possessing an antitumor activity which is recovered from the liquid portion which comes from cooking of raw scallop with a hot aqueous solvent or with the vapor of such solvent and which has the following characteristics:-

(1) Appearance: White, powdery solid.
(2) Solubility: Soluble easily in water, but insoluble in organic solvents such as methanol, ethanol and acetone.
(3) Acidic or basic nature: Amphoteric electrolyte having an isoelectric point of pH 5.5.
(4) Infrared absorption spectrum (pelleted in KBr): With characteristic absorption peaks at 3500~3300, 1660 and 1550 cm$^{-1}$.
(5) Ultraviolet absorption spectrum in an aqueous solution: With a characteristic absorption peak $\lambda_{max}$ H$_2$O at 255 nm.
(6) Color reactions: Positive in biuret reaction, xanthoproteic reaction, phenolic reagent reaction according to Lowry-Folin method, anthrone-sulfuric acid reaction, phenol-sulfuric acid reaction and cysteine-sulfuric acid reaction.
(7) Average molecular weight: About 470,000 as measured by gel-electrophoresis.

BRIEF DESCRIPTION OF THE DRAWINGS

In the accompanying drawings:-

FIG. 1 shows an elution pattern depicted in gelfiltration chromatography carried out in a step for isolating a water-soluble glycoprotein substance according to this invention, more concretely an elution pattern depicted in gel-filtration chromatography of an intermediate substance separated by DEAE ion-exchanging chromatography in Example 2 hereinafter given, wherein the abscissa axis represents fraction numbers of the eluate, the ordinate axis represents absorbance shown as optical density, the white circles (S) show absorbance at wave length of 490 nm of each eluate fraction colored by the method of Dubois et al. (see J. Anal. Chem., 28, 350-356 (1956)) as an indicator of the carbohydrate content of fractions and the black circles (P) show absorbance at wave length of 750 nm of each eluate fraction colored by Lowry method as an indicator of the protein content of fractions.

DETAILED DESCRIPTION OF THE INVENTION

The novel glycoprotein substance according to this invention is derived from natural sources, particularly from the liquid portion coming from the cooking of raw scallop in an aqueous solvent or with vapor of such solvent, and is a homogeneous substance of high average molecular weight which shows a single peak both in liquid chromatography and in gelfiltration chromatography and shows a single band in electrophoresis such as disc electrophoresis, which corresponds to Sample E obtained in Example 2 hereinafter given. This substance has the following physico-chemical properties:-

(1) Elementary analysis: C 40.2; H 6.4; N 7.1; S 0.1; P 0.1; Ash 1.0% by weight.

(2) Molecular weight: About 470,000 as average molecular weight obtained by SDS-5% polyacrylamide gel-electrophoresis wherein comparison is made between Rf value (relative mobility) of the sample and those values of standard substances to estimate the molecular weight of the former correlatively.

(3) Rf value (relative mobility) in electrophoresis: A single peak band at Rf value of 0.04 relative to that of Bromophenol blue as standard in electrophoresis on 7.5% acrylamide gel in a buffer solution at pH 8.0.

(4) Melting point: No definite melting point and no definite decomposition point are seen, but some decomposition is observed at 240° C.

Figure 3:
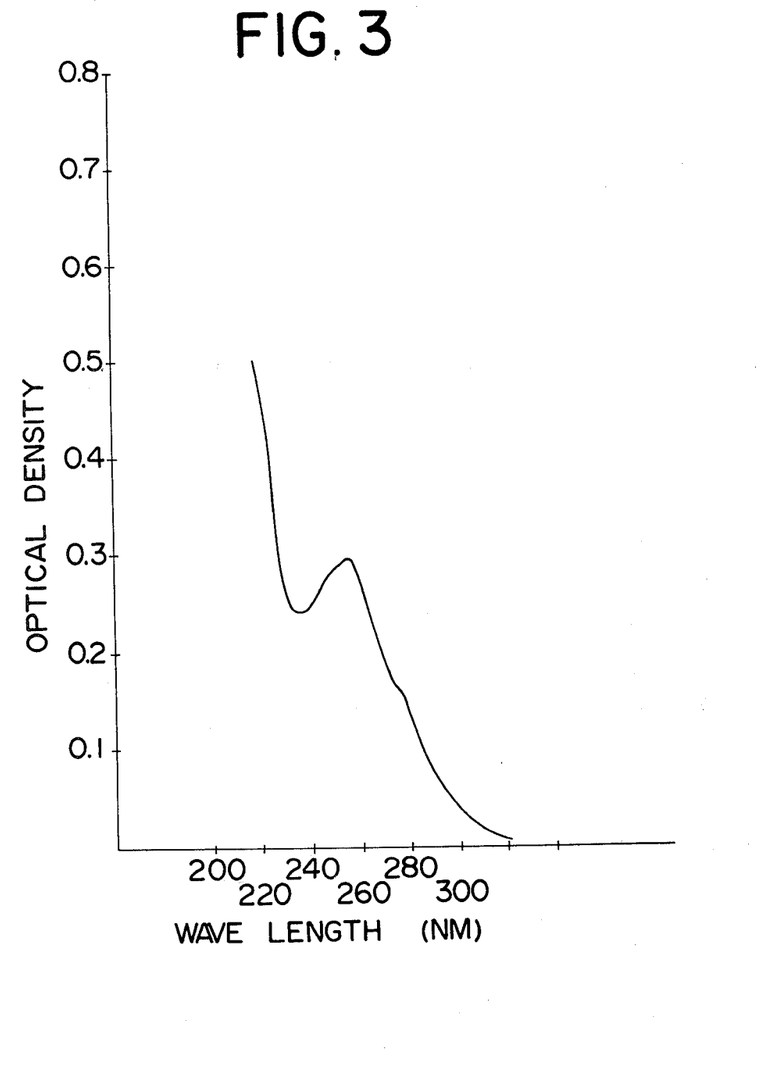

(5) Ultraviolet absorption spectrum: An aqueous solution of the sample reveals the UV absorption spectrum as shown in FIG. 3 with a characteristic absorption peak $\lambda_{max}$ H$_2$O at 255 nm.

Figure 2:
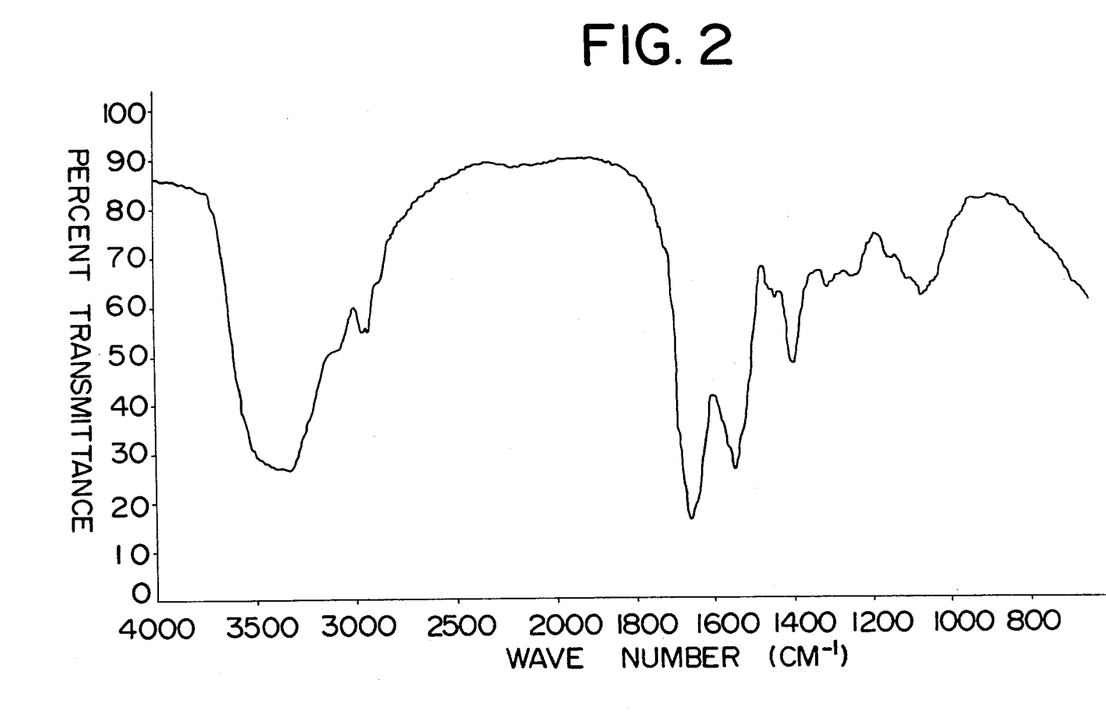
FIG. 2 shows infrared absorption spectrum of a sample of glycoprotein substance according to this invention (Sample E obtained in Example 2 hereinafter given) pelleted in KBr and FIG. 3 shows ultraviolet absorption spectrum of the same sample in the form of a 0.1 mg/ml aqueous solution.

(6) Infrared absorption spectrum (pelleted in KBr): As shown in FIG. 2 with characteristic absorption peaks at 3500~3300, 2960, 2940, 1660, 1550 and 1400 cm$^{-1}$.

(7) Color reactions: Positive in biuret reaction, xanthoproteic reaction, phenolic reagent reaction according to Lowry-Folin method, anthrone-sulfuric acid reaction, phenol-sulfuric acid reaction and cysteine-sulfuric acid reaction.

(8) Acidic or basic nature: Amphoteric electrolyte having an isoelectric point of pH 5.5.

(9) Solubility: Soluble in water, but insoluble in organic solvents such as methanol, ethanol and acetone.

(10) Appearance: White, powdery solid.

(11) Carbohydrate content: 29.4% by weight calculated in terms of glucose when measured by the phenol-sulfuric acid method.

(12) Amino acids in hydrolyzate: When hydrolyzed in 6 N HCl at 105°~110° C. for 24 hours, the resulting hydrolyzate contains at least the following amino acids:-aspartic acid, hydroxyproline, threonine, serine, glutamic acid, proline, glycine, alanine, cysteine, valine, methionine, isoleucine, leucine, tyrosine, phenylalanine, histidine, 3-methylhistidine, hydroxylysine, lysine, arginin.

(13) Carbohydrates in hydrolyzate: When hydrolyzed in 1N HCl at 80° C. for 3 hours, the hydrolyzate shows by gas chromatography to contain at least the following neutral carbohydrates:- fructose, galactose, fucose, mannose.

Judging from the above-mentioned properties of the sample substance, it is believed that the substance according to this invention consists essentially of a water-soluble, high molecular weight glycoprotein.

As above-mentioned, the substance according to this invention has a high average molecular weight of about 470,000 and a relatively low isoelectric point of pH 5.5. On the other hand, the concentrate or dry powder derived from the waste liquid portion coming from cooking of raw scallop contains a variety of amphoteric electrolytes having different isoelectric points, thus exhibiting a strong pH-buffering action. When dissolved in distilled water, the concentrate or dry powder shows a pH of about 5.5. When dissolved in 0.1 M phosphate buffer solutions having different pH values lower than 7.0, the concentrate or dry powder shows a pH of 5.2~6.0 with a tendency of lowering the pH value with the increase in the amount of concentrate or dry powder dissolved. Possibly owing to these behaviors of the concentrate or dry powder, substances having an isoelectric point of pH of around 5.5 such as the substance according to this invention could not be eluted or dissolved in an eluent or solvent used during various fractionation and isolation operations for the purpose of recovering water-soluble glycoprotein substances possessing useful antitumor activities from the concentrate or dry powder because those substances would form insoluble precipitate or adsorb on various gels used during such operations. This is, we think, the reason why the substance according to this invention could not have been detected until now.

As explained hereinbefore, this invention is based on the discovery during our investigations on antitumor substances contained in the concentrate or dry powder in question that fractions corresponding to such high molecular weight substances as about 450,000~500,000 exhibit a very high antitumor activity. This is quite unknown yet, thus unexpected in the art.

As a result of our careful examination of all the above-mentioned properties of the substance of this invention in comparison with those properties of known antitumor substances derived from shellfish given in literature including typically Japanese Patent Publication No. 8088/82, Japanese Patent KOKAI Nos. 41314/79 and 41315/79, U.S. Pat. application Ser. No. 404,971 and Journal of National Cancer Institute, 60, 6, 1499-1500 (1978), we believe that the substance according to this invention is not identical with any of those disclosed in literature but novel and useful as antitumor agent.

The glycoprotein substance according to this invention can be derived from scallop. To be concrete, this substance may be prepared starting from the liquid portion to be discarded as waste which comes from cooking of raw scallop with a hot aqueous solvent or with the vapor of such solvent. The liquid portion which includes a condensate obtained in the cooking of raw scallop may be used as it is or in a concentrate or a dry powder derived therefrom. The isolation of the substance from the said liquid portion and the purification of the substance thus isolated may be effected in a manner known per se, that is by applying any one of or any combination of two or more of known means usually used for the isolation and purification of protein and carbohydrate substances in the art, such as, for example, centrifugation, dialysis, ultrafiltration, gel-filtration chromatography, ion-exchange chromatography, chromatofocusing, ion exchange resin-treatment, affinity chromatography, liquid chromatography, electrophoresis, isoelectric focusing, salting-out, precipitation with organic solvent, isoelectric point-precipitation, vacuum concentration, hot air-drying and freeze-drying. The sequence of two or more steps to be adopted for the isolation and purification of the object substance may be arranged as desired and repetition of certain treatment(s) may be done, if necessary.

According to one aspect of this invention, there is provided a process for the preparation of a glycoprotein substance having an average molecular weight of about 470,000 and possessing an antitumor activity from scallop which comprises recovering the liquid portion which comes from cooking of raw scallop with a hot aqueous solvent or with vapor of such solvent and which is to be discarded as waste, concentrating the liquid portion thus recovered to a smaller volume or to dryness to yield a concentrate or dry powder, dissolving the concentrate or dry powder in water or an aqueous solvent to form an aqueous solution thereof and subjecting the aqueous solution to a series of treatments comprising ion exchange chromatography with a basic anion exchanger and molecular weight-fractionating treatments (i.e. fractionating treatments for isolating a fraction of aimed molecular weight range) comprising gel-filtration and electrophoresis, in any desired sequence, whereby isolating a fraction consisting essentially of a glycoprotein substance which is adsorbable on a basic anion exchanger and which has an average molecular weight of about 470,000.

A preferred embodiment of the process for the preparation of the glycoprotein substance according to this invention comprises the steps of recovering the liquid portion which comes from cooking of raw scallop with a hot aqueous solvent or with vapor of such solvent and which is to be discarded as waste, concentrating the liquid portion thus recovered to a smaller volume or to dryness to yield a concentrate or dry powder, dissolving the concentrate or dry powder in water or an aqueous solvent to form an aqueous solution thereof and subjecting the aqueous solution to ion exchange chromatography with a basic anion exchanger to recover a fraction which is adsorbed on the exchanger followed by subjecting the fraction to molecular weightfractionating treatments comprising gel-filtration and electrophoresis whereby to isolate a fraction consisting essentially of a glycoprotein substance having an average molecular weight of about 470,000. According to the most preferred embodiment of the process according to this invention, the treatments of the concentrate or dry powder are carried out in a buffer solution having a strong buffering action.

The liquid portion coming from cooking of raw scallop to be used as starting material according to the process of this invention may include those by-produced when fresh or raw scallop which may have been heated if desired, is cooked or heat-treated in a hot aqueous solvent or with vapor of such solvent for the purpose of obtaining edible portions thereof. The hot aqueous solvent to be used as heating medium may include hot or boiling water, steam and other hot aqueous solvents such as saline solution and sea water and vapor of such solvents.

In order to take up edible portion of scallop and to recover the liquid portion containing antitumor substances by cooking or heat-treating (hereinafter referred to as "cooking"raw scallop in a hot aqueous solvent or with vapor of such solvent, the cooking operation is effected in one or more steps, in each of which the scallop is brought into contact with a hot aqueous solvent in the form of liquid and/or vapor which serves as both heating medium and extracting solvent. The method of contact between scallop and hot aqueous solvent may be selected as desired, for example from among those of direct exposure to solvent vapor, direct pouring of hot solvent and immersion into hot solvent. The hot aqueous solvent may be used in the form of either liquid or vapor or both.

For the purpose of this invention, the raw scallop may be used in its entirety, i.e. in the shell, or a shelled form with or without liver, as desired. According to this invention, therefore, all the edible portions, i.e. meat, ligament and the like, of scallop can be used for food after the cooking operation because no cutting or grinding of scallop is required for cooking.

Usually, the cooking may be carried out at a temperature of about 50°~120° C., preferably about 60°~120° C. for a period of time of about 3~120 minutes, preferably about 5~60 minutes.

The liquid portion coming from the cooking of raw scallop as above-mentioned, which contains antitumor substances, may be concentrated to a smaller volume or to dryness to yield a concentrate or dry powder in a known manner, e.g. by heating in vacuo, hot air-drying or freezedrying. Hot air-drying such as one using a spray drier is preferred in order to prevent or minimize the deterioration of the object substances because the contact (residence) time is as short as about 5~80 seconds under conditions of the hot air temperature of about 200°~350° C. at the inlet and of about 80°~170° C. at the outlet.

The isolation of the glycoprotein substance of this invention from the concentrate or dry powder thus obtained and the subsequent purification may be carried out, according to one embodiment of this invention, as follows:

The concentrate or dry powder is dissolved in an aqueous solvent and the solution is centrifuged or filtered to remove insoluble matters and then desalted by gel-filtration or dialysis, for example. The resulting solution is subjected to ion-exchange chromatography by passing through a column of a basic anion exchanger such as an ion-exchanging gel having such dissociating group as diethylaminoethyl group or aminoethyl group with the elution of the adsorbed fraction being effected with aqueous NaCl solutions (about 0.07~0.4 mol/l) as eluents. The eluted fractions are subjected to molecular weight-fractionating treatment such as vertical slab gel-electrophoresis and gel-filtration to obtain the object substance having an average molecular weight of about 470,000. Optional step or steps for the purposes of desalting and concentration may be inserted at any suitable point between steps involved in the process, if desired. The desalting may be effected typically by dialysis or gel-filtration and the concentration may be carried out typically by heating in vacuo or freeze-drying. In order to prevent the deposition of the object substance into insoluble precipitate, these treatments should preferably be carried out in a buffer solution having a strong buffering action, for example a phosphate buffer solution having a concentration of about 0.05 M or higher, preferably about 0.1 M or higher. The term "a phosphate buffer solution" used herein means an aqueous solution of a phosphate mixture of potassium dihydrogenphosphate and disodium hydrogenphosphate.

The water-soluble glycoprotein substance according to this invention is useful as antitumor agent with such particular advantages that it has a wide antitumor spectrum without appreciable cytotoxicity and that a noticeable tumor regression effect can be achieved by adopting various administration routes which are normally applied in the management of cancers. Thus, intratumor, subcutaneous, intraperitoneal, intracutaneous, intramuscular, or intravenous injections, if necessary, oral and rectal administrations, or in external applications, coating, instillation and other methods of administration are feasible.

The process of this invention is also advantageous in view of environmental protection in that a substantial amount of organic substances contained in the liquid portion coming from cooking of raw scallop can be recovered as useful product with the result that the organic contents of the waste liquor are substantially reduced.

In the tests hereinafter given, the evaluation of antitumor activity of the antitumor substances isolated was made by the following method unless otherwise stated.

Sarcoma 180 tumor cells are maintained in ICR mice, 5~7 weeks old, in an ascites form. Four millions of Sarcoma 180 cells are subcutaneously transplanted into the right inguinal region of female ICR mice, 6 weeks old. Then, the test samples dissolved or suspended in a physiological saline in adequate concentrations (injection volume, 0.1 ml) are subcutaneously injected into the left inguinal region of the mice under test three times every second day. Three weeks after the tumor cell transplantation, the diameter of growing solid tumor or the weight of solid tumor removed are measured and the data obtained are compared with those of control group wherein a physiological saline solution is used in place of the test sample solution.

The inhibition ratio and complete tumor regression are calculated by the following formula:

$$\text{Inhibition ratio (\%)} = \left(1 - \frac{\text{Average tumor weight of the treated group}}{\text{Average tumor weight of the control group}}\right) \times 100$$

$$\text{Complete tumor regression} = \frac{\text{The number of mice showing complete tumor regression}}{\text{The total number of mice tested}}$$

This invention is now illustrated with reference to the following Examples to which the invention is in no way limited.

EXAMPLE 1

One part (by weight) of raw scallop shellfish (*Patinopecten yessoensis*) in the shells was charged into a vessel continuously, into which 0.10 parts (by weight) of superheated steam at 105°~110° C. was blown so that the raw scallop shellfish was directly exposed to the blown steam and cooked at 90°~100° C. for 10 minutes. At the bottom of the vessel, there was collected a volume of the water condensate containing the active substances dissolved therein as a first crop solution of the active substances. The outer shells of raw scallop shellfish used as the starting material had about 0.1 parts (by weight) of the infesting acorn shells attached thereto. The first crop solution of the active substances was removed out of said vessel and then slowly cooled down from 90° C. to 50° C. and then immediately passed through a spraying drier. This drier had an inlet through which a stream of hot air at 280° C. was passed into the drier, as well as an outlet through which the effluent gases were discharged from the drier at a temperature of 125° C. The first crop solution of the active substances was dried in the drier in a retention time of 45 seconds to give a first crude powder of the active substances (Sample 1*a*) in a yield of 0.27% by weight based on the raw scallop employed.

Then, the ligament portions were removed from the scallop by means of knife. The scallop ligament so collected (50 kg) was placed into a volume (450 kg) of a boiling saline solution containing 10% by weight of sodium chloride in water, boiled in the boiling saline solution for 20 minutes and then removed therefrom. With the same saline solution, further three 50 kg portions of the scallop ligament were treated in the same manner as above. This saline solution was recovered as a second crop solution of the active substances. The second crop solution of the active substances was slowly cooled down from 90° C. to 40° C. and dried in the same manner as that for the first crop solution of the active substances to give a second crude powder of the active substances (Sample 1*b*) in a yield of 0.20% by weight based on the scallop employed.

Two parts by weight of the first crude powder (Sample 1*a*) were mixed with one part by weight of the second crude powder (Sample 1*b*) to give a third crude powder of the active substances (Sample 1*c*).

Test A

The third crude powder, i.e. Sample 1*c*, (1200 g) obtained as above was dissolved in 6 l of a 0.01 M phosphate buffer solution (pH 7.5) and the resulting solution was centrifuged at 10,000 G for 20 minutes to remove the insoluble matters therefrom. A 3 l portion of the supernatant solution was charged for the desalting purpose into a column (15 cm in height; 16 l in volume) of Sephadex G-25 (a product of Pharmacia Fine Chemicals Co., which is a gel for gelfiltration obtained by three-dimensionally crosslinking dextran with epichlorohydrin and which is capable of fractionating substances of molecular weights in the range of about 500~5000) which had been well equilibrated with distilled water. Then, a further amount of distilled water was passed through the column as developer and the eluate was continuously passed through a conductometric titration cell to detect the point at which the electric conductivity of the eluate was increased due to the presence of inorganic salts therein, so that fractions eluted by that point were collected. The fractions so collected were passed through a column of an ion exchanging gel, DEAE-Sepharose CL-6B (a product of Pharmacia Fine Chemicals, Co. which is a gel obtained by three-dimensionally crosslinking agarose with 2,3-dibromopropanol followed by introducing diethylaminoethyl group through an ether linkage and which has chlorine ion as counter ion, the upper limit of molecular weights to be fractionated of about $1 \times 10^6$ and the total exchange capacity of $15 \pm 2$ meq/100 ml) which had been well equilibrated with distilled water whereby to remove non-adsorptive substances. The column was then eluted with an eluent comprising a 0.01 M phosphate buffer solution (pH 7.5) containing 0.25 M NaCl. The eluted fractions containing glycoprotein substances of different molecular weights were collected and concentrated in vacuo below 30° C. The resulting concentrate was dialyzed against distilled water for 48 hours for desalting and then freeze-dried to yield 6.15 g of a glycoprotein powder (A).

Another 3 l portion of the supernatant solution derived from Sample 1*c* was charged for the desalting purpose into a column of Sephadex G-25 which had been equilibrated with a 0.1 M phosphate buffer solution (pH 7.5), with the elution being effected by passing through the column a further amount of the same 0.1 M phosphate buffer solution as that used above as developer. The desalted fractions were collected and passed through a column of DEAE-Sepharose CL-6B which was the same as above, but which had been equilibrated with the same 0.1 M phosphate buffer solution as that used above whereby to remove non-adsorptive substances. The column was then eluted with an eluent comprising a 0.1 M phosphate buffer solution (pH 7.5) containing 0.2 M NaCl and the eluted fractions were treated in the same manner as that used to treat the corresponding eluted fractions derived from the first 3 l portion above to yield 5.83 g of a glycoprotein powder (B).

The antitumor activity of each of powder (A) and powder (B) thus obtained was examined according to the method defined above and the results are shown in Table 1.

TABLE 1

| Sample | Dose (mg/mouse × times*) | Average weight of tumors (g) | Inhibition ratio (%) | Complete regression |
|---|---|---|---|---|
| Control | — | 9.25 | — | 0/8 |
| A | 10 × 3 | 1.15 | 87.6 | 0/5 |
| B | 10 × 3 | 1.20 | 87.0 | 0/5 |

*Administered into the tumor site on the 5th, 7th and 9th days after the tumor cell transplantation.

Test B

One gram each of powder (A) and powder (B) obtained in Test A above was dissolved in 20 ml of a 0.1 M phosphate buffer solution (pH 7.5) and each solution prepared was charged into a column (60 cm in height and 2.5 cm in inner diameter) of Sephacryl S-400 (a product of Pharmacia Fine Chemicals Co. which is a gel obtained by crosslinking allyldextran with N,N'-methylenebisacrylamide and which is capable of fractionating substances of molecular weights in the range of $1\times10^4 \sim 2\times10^6$) which had been well equilibrated with the same 0.1 M phosphate buffer solution as that used above. The column was eluted with the same 0.1 M phosphate buffer solution as that used above (pH 7.5) to collect the eluate as fraction (A) for powder (A) and as fraction (B) for powder (B), respectively.

Another 1 g portion of powder (B) was dissolved in 20 ml of a 0.01 M phosphate buffer solution (pH 7.5) and the solution was charged into a column of Sephacryl S-400 which was similar to that used above but which had been well equilibrated with distilled water. The column was eluted with distilled water whereby to collect the eluate as fraction (C).

In order to decide the ranges of molecular weights to be fractionated from the three fractions (A), (B) and (C), a calibration curve was depicted from elution data of known standard substances such as blue dextran, thyroglobulin, ferritin, aldolase, ovalbumin and ribonuclease A on the column of Sephacryl S-400 same as above. Thus, the three molecular weight fractions, namely, fraction (1) with molecular weights higher than 300,000, fraction (2) with molecular weights of 100,000~300,000 and fraction (3) with molecular weights lower than 100,000, were decided relatively using the calibration curve.

The three fractions (A), (B) and (C) each were further fractionated into the fractions (1), (2) and (3), respectively and the respective fractions were dialyzed against distilled water followed by freeze-drying to yield nine powders A-1, A-2, A-3, B-1, B-2, B-3, C-1, C-2 and C-3. The yield of each powder obtained is shown in Table 2.

TABLE 2

| Fraction used | Developer | Fraction 1 | Fraction 2 | Fraction 3 | Total |
|---|---|---|---|---|---|
| A | Buffer solution | A-1: 0.11 g | A-2: 0.42 g | A-3: 0.22 g | 0.75 g |
| B | Buffer solution | B-1: 0.20 g | B-2: 0.47 g | B-3: 0.24 g | 0.92 g |
| C | Distilled water | C-1: 0.09 g | C-2: 0.45 g | C-3: 0.26 g | 0.81 g |

The results shown in Table 2 showed a considerable difference in the yield of fraction 1 having molecular weights higher than 300,000 among A, B and C series experiments which were carried out by using the same starting material and substantially the same method except for the use of different developers. Therefore, the evaluation of antitumor activity was made on all the nine powder fractions according to the method defined as above. The results are shown in Table 3.

TABLE 3

| Sample tested | Dose (mg/mouse × times*) | Average weight of tumors (g) | Inhibition ratio (%) | Complete regression |
|---|---|---|---|---|
| Control | — | 10.43 | — | 0/8 |
| A-1 | 5 × 3 | 5.83 | 44.1 | 0/5 |
| A-2 | " | 2.73 | 73.8 | 0/4 |
| A-3 | " | 2.68 | 74.3 | 0/5 |
| B-1 | " | 1.95 | 81.3 | 1/5 |
| B-2 | " | 2.43 | 76.7 | 0/4 |
| B-3 | " | 2.15 | 79.3 | 0/4 |
| C-1 | " | 6.28 | 39.8 | 0/4 |
| C-2 | " | 2.80 | 73.2 | 0/5 |
| C-3 | " | 2.53 | 75.7 | 0/4 |

*Administered into the tumor site on the 5th, 7th and 9th days after the tumor cell transplantation.

There was observed no appreciable difference in antitumor activity between powders A and B in Test A. In contrast, comparison among the highest molecular weight powder fractions A-1, B-1 and C-1 in Test B clearly showed that fraction B-1 contained a substance exhibiting the highest antitumor activity, whereas fraction C-1 contained little or no such substance of the highest antitumor activity which must have been contained originally in powder B. This suggested that the method used to recover fraction C from powder B was not appropriate for the recovery of glycoprotein substances having molecular weights higher than 300,000 possibly due to their conversion or inclusion into insoluble materials during the treatments or for some other reason.

Since there was nothing reported or even suggested so far about that fractions of molecular weights higher than 300,000 derived from shellfish contain substance or substances possessing antitumor activities, we did not expect to be able to isolate such useful substance(s) from the concentrate or dry powder derived from scallop, but now found as above that such high molecular weight substances which are difficult to keep in solution during chromatographic treatments could be successfully treated by ion-exchange chromatography, gel-filtration chromatography and the like if eluent or developer to be used for said treatments is of a strong pH buffering action. Based on these findings, we further continued our study on such fractions of molecular weights higher than 300,000 and finally ascertained the entity of substance exhibiting the highest antitumor activity contained in such high molecular weight fractions to be a glycoprotein substance which shows a single band in 7.5% polyacrylamide gel-electrophoresis and which has an average molecular weight of about 470,000.

EXAMPLE 2

(a) The third crude powder, i.e. Sample 1c, (600 g) obtained in Example 1 was dissolved in 3 l of a 0.1 M phosphate buffer solution (pH 7.5) and the resulting solution was centrifuged at 10,000 G for 20 minutes to remove insoluble matters therefrom and then charged for the desalting purpose into a column (15 cm in height; 16 l in volume) of Sephadex G 25 which had been well equilibrated with the same 0.1 M phosphate buffer solution as that used above. Then, a further amount (20 l/hr) of the same 0.1 M phosphate buffer solution was passed through the column as developer and the eluted fractions free from inorganic salts were collected by monitoring the electric conductivity of the eluent in the same manner as that used in Test A of Example 1. The fractions thus desalted were then passed through a column of 16 l of a DEAE-Sepharose CL-6B ion-exchanging gel which had been well equilibrated with the same 0.1 M phosphate buffer solution as that used above whereby to remove non-adsorptive substances. The column was then washed well with the same 0.1 M phosphate buffer solution as that used above and eluted with an eluent comprising the same 0.1 M phosphate buffer solution (pH 7.5) as that used above but containing 0.2 M NaCl. The eluted fractions were collected and concentrated in vacuo below 30° C. to a volume (2 l) of about one-fifth of the original volume. The concentrated eluate was dialyzed against distilled water for 48 hours for desalting and then freeze-dried to yield 6.08 g of a glycoprotein powder (C) (yield: 1.01% based on the liquid portion coming from cooking of raw scallop).

Figure 1:
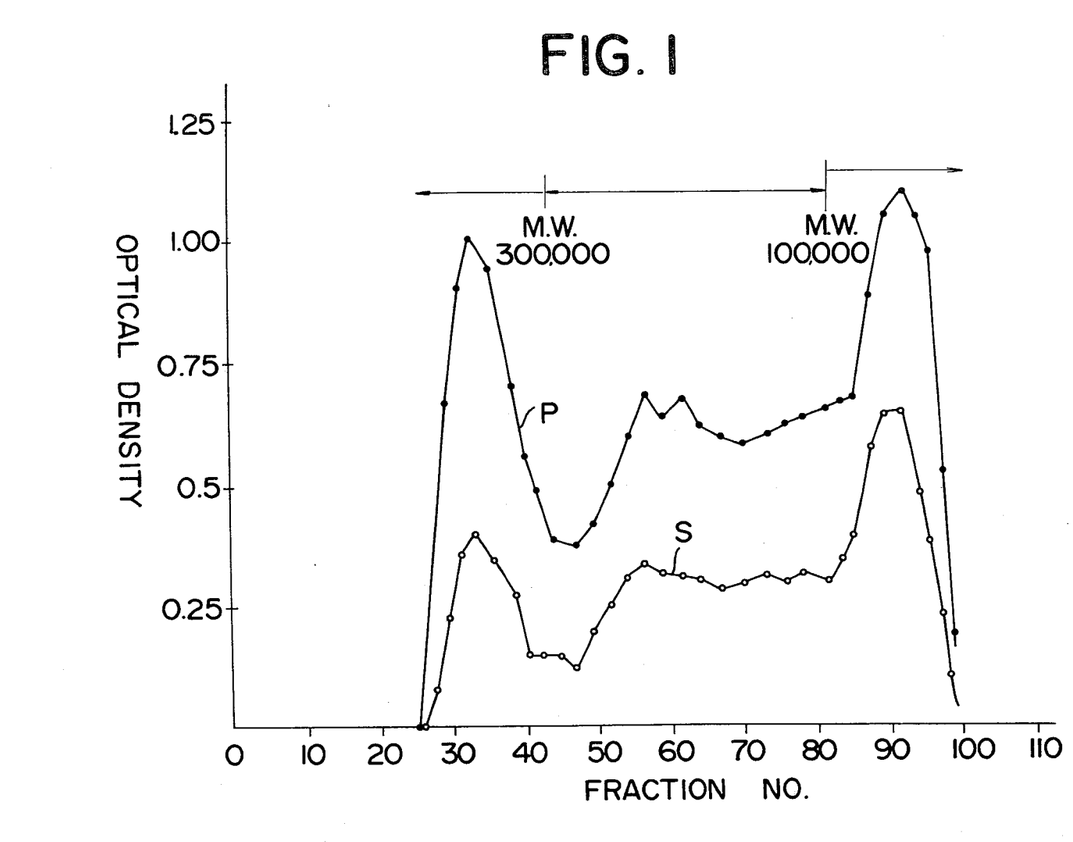

A 2 g portion of powder (C) thus obtained was dissolved in 30 ml of the same 0.1 M phosphate buffer solution (pH 7.5) as that used above and the resulting solution was charged into a column (2.5 cm in inner diameter and 60 cm in length) of Sephacryl S-400 which had been well equilibrated with the same 0.1 M phosphate buffer solution as that used above and chromatographed with the same 0.1 M phosphate buffer solution as that used above as eluent. Fractions corresponding to those comprising substances having molecular weights higher than 300,000 which were relatively estimated by a calibration curve depicted from elution data of known standard substances on the same Sephacryl S-400 column as above were collected and the fractions so collected were dialyzed against distilled water for 48 hours followed by freeze-drying to yield 275 mg of powder (D). The elution pattern depicted in this gel-filtration chromatography is given in FIG. 1.

A 20 mg portion of powder (D) was dissolved in 1.5 ml of a 0.1 M phosphate buffer solution (pH 8.0) and the resulting solution was subjected to vertical slab gel-electrophoresis using 7.5% polyacrylamide gel in the same 0.1 M phosphate buffer solution as that used above under the condition of constant current of 50 mA for 4 hours whereby to fractionate substances according to molecular weights. "Polyacrylamide gel-electrophoresis" is electrophoresis using a gel bed (14 cm × 14 cm × 2 mm) prepared by polymerizing a liquid mixture comprising acrylamide monomer, N,N'-methylenebisacrylamide crosslinking agent and a polymerization catalyst. "7.5% polyacrylamide" in the electrophoresis means the concentration of acrylamide used in the liquid mixture to be polymerized being 7.5% by weight. This electrophoresis operation was repeated for two further 20 mg portions of powder (D). In each of three operations, the portion of gel which showed Rf values of 0~0.08 relatively to Bromophenol blue at pH 8.0 was cut off and all three portions were finely divided in 100 ml of an eluent comprising a 0.1 M phosphate buffer solution (pH 7.5) containing 1 M NaCl on a homogenizer and filtered. The gel separated on the filter was washed with further amount of the eluent and the washings were combined with the filtrate and the combined liquor was concentrated, freeze-dried, dialyzed for 48 hours and finally freeze-dried to yield 12 mg of powder (E). (b) Powders (D) and (E) obtained in Example 2(a) above were evaluated on their antitumor activities according to the test method defined hereinbefore with the following results:

TABLE 4

| Sample | Dose (mg/mouse × times*) | Average weight of tumors (g) | Inhibition ratio (%) | Complete regression |
|---|---|---|---|---|
| Control | — | 8.95 | — | 0/9 |
| D | 5 × 3 | 1.48 | 83.4 | 1/4 |
|   | 1 × 3 | 1.92 | 78.5 | 0/5 |
| E | 1 × 3 | 0.53 | 94.1 | 2/5 |
|   | 0.5 × 3 | 0.42 | 95.3 | 1/4 |
|   | 0.2 × 3 | 0.45 | 94.9 | 2/5 |

*Administered into the tumor site on the 5th, 7th and 9th days after the tumor cell transplantation.

(c) The average molecular weight of powder (E) obtained in Example 2(a) above was measured by SDS-5% polyacrylamide gel-electrophoresis relatively to molecular weight reference standard materials such as blue dextran, thyroglobulin, ferritin, aldolase, ovalbumin and ribonuclease A in a usual manner. "SDS-polyacrylamide gel-electrophoresis" is electrophoresis using a gel prepared by polymerizing a liquid mixture comprising acrylamide monomer, N,N'-methylenebisacrylamide crosslinking agent, a polymerization catalyst and sodium dodecyl sulfate (SDS). The electrophoresis of powder (E) showed a single band with color development at the position corresponding to about 470,000 (accuracy: ±30,000).

(d) The isoelectric point of powder (E) obtained in Example 2(a) was measured by isoelectric focusing over pH range of 4.0~6.0 under the condition of constant power of 20 W using Servalyt Precotes 4-6 (a product of Serva AG which is a gel comprising Servalyt AG 4-6 and 5% polyacrylamide gel) as precoated film for isoelectric focusing. Servalyt AG 4-6 is a product of Serva AG, which is a mixture of amphoteric electrolytes comprising aliphatic compounds having molecular weights ranging 500~800 and containing secondary and tertiary nitrogen-containing groups such as guanid group, sulfonic acid group and phosphonic acid group and is used as carrier ampholytes to give a pH gradient of 4.0~6.0. The isoelectric point of powder (E) was measured relatively to those of known substances as reference standards by comparing their migration bands and estimated to be about pH 5.5.

(e) Physico-chemical properties of powder (E) were also measured, which are as shown hereinbefore.

EXAMPLE 3

(a) Antitumor activity of powder (E) obtained in Example 2, when administered not only into the tumor site but also through other routes, was examined by the following method.

Sarcoma 180 tumor cells (about $6 \times 10^6$ cells) were subcutaneously transplanted into the right groin of female ICR mice, 6 weeks old. Powder (E) was dissolved in a physiological saline in appropriate concentrations and each of the resulting test solutions (pH 7.0; injection volume 0.1 ml) was injected on 5th, 7th and 9th days after the tumor cell transplantation. The injections were effected through several routes, namely directly into the tumor site, intravenously into the tail, intraperitoneally and subcutaneously into the opposite groin. After the lapse of 5 weeks from the transplantation, the mice were killed and the solid tumors were dissected out and weighed. The results were compared with those of control group wherein a physiological saline solution was administered in place of each test sample. Inhibition ratio (%) and complete regression were calculated as defined hereinbefore. The results are shown in Table 5.

TABLE 5

| Administration route | Dose (mg/mouse × times) | Average weight of tumors (g) | Inhibition ratio (%) | Complete regression |
|---|---|---|---|---|
| Control | — | 9.23 | — | 0/7 |
| Directly into tumor site | 0.1 × 3 | 0.45 | 95.1 | 1/5 |
| Intravenously into tail | 0.2 × 3 | 0.32 | 96.5 | 3/4 |
|  | 0.1 × 3 | 1.52 | 83.5 | 0/4 |
| Subcutaneously into groin | 0.2 × 3 | 0.43 | 95.3 | 1/5 |
|  | 0.1 × 3 | 0.51 | 94.4 | 2/5 |
| Intraperitoneally | 0.2 × 3 | 0 | 100 | 3/3 |
|  | 0.1 × 3 | 1.11 | 88.0 | 1/4 |

The results given in Table 5 demonstrate that powder (E) isolated in Example 2 is remarkably effective in degeneration and complete regression of Sarcoma 180 solid tumors through various routes for administration, that is in tumor site, intravenously, intraperitoneally and subcutaneously.

(b) Direct cytotoxicity of powder (E) was also examined against L 5178 Y Lymphoma cells in vitro, but there was found no appreciable cytotoxicity.

The test on cytotoxicity was effected as follows:

L 5178 Y ($5 \times 10^5$ cells/ml) were suspended in a tissue culture medium, Eagle MEM (containing 15% calf serum) and the suspension, after the addition of test sample in the concentrations as undermentioned thereto, was incubated in an incubator under 5% $CO_2$ in air at 37° C. for 48 hours. Then, the effect of test sample on target cell proliferation was estimated with a phase-contrast microscope. A physiological saline solution and mitomycin C were used as control and reference, respectively. The results of the direct cytotoxicity test are shown in Table 6.

TABLE 6

| Sample | Concentration of sample (μg/ml) | Growth inhibition (%) |
|---|---|---|
| Powder (E) of this invention | 40 | 0 |
|  | 200 | 0 |
| Mitomycin C | 20 | 30 |
|  | 100 | 68 |
| Control (Physiological saline solution) |  | 0 |

EXAMPLE 4

This Example illustrates the antitumor activity of powder (E) isolated in Example 2 on several solid tumors other than Sarcoma 180 solid tumor.

The tumor cells ($4 \times 10^6$ cells) of each of Ehrlich carcinoma, Leukemia SN-36, NTF reticulum cell sarcoma and methylcholanthrene-induced Fibrosarcoma which were maintained in ICR female mice or Balb/c mice (for Fibrosarcoma only) were subcutaneously transplanted into one groin of another group of female, 6 weeks aged ICR mice or Balb/c mice correspondingly. One week after the transplantation, the tumor cells were confirmed to have grown to solid tumors. Then, a solution in physiological saline of powder (E) was directly injected into the tumor site at a dose of 0.2 mg/mouse three times on alternate days. Five weeks after the tumor cell transplantation, the solid tumors were dissected out and weighed. The results were compared with that of control group wherein a physiological saline solution was administered in place of the test solution. Inhibition ratio (%) and complete regression were calculated as hereinbefore defined. The results are shown in Table 7.

TABLE 7

|  | Ehrlich carcinoma | SN-36 | NTF | Fibrosarcoma |
|---|---|---|---|---|
| Inhibition ratio (%) | 100 | 83.9 | 93.8 | 100 |
| Complete regression | 4/4 | 2/4 | 3/4 | 4/4 |

EXAMPLE 5

The procedure described in Example 2 was repeated except that Sample 1a was used in place of Sample 1c, yielding an antitumor substance consisting essentially of a water-soluble glycoprotein substance having an average molecular weight of about 470,000. The physico-chemical properties and antitumor activity of this substance were substantially the same as those of powder (E) isolated in Example 2.

EXAMPLE 6

The procedure described in Example 2 was repeated except that Sample 1b was used in place of Sample 1c, yielding an antitumor substance consisting essentially of a water-soluble glycoprotein substance having an average molecular weight of about 470,000. No difference could be found between the physico-chemical properties and antitumor activity of this substance and those of powder (E) isolated in Example 2.

What we claim is:

1. A glycoprotein substance possessing an antitumor activity which is recovered from the liquid portion which comes from cooking of raw scallop with a hot aqueous solvent or with the vapor of such solvent and which has the following characteristics:-
   (1) Appearance: White, powdery solid.
   (2) Solubility: Soluble easily in water, but insoluble in organic solvents such as methanol, ethanol and acetone.
   (3) Acidic or basic nature: Amphoteric electrolyte having an isoelectric point of pH 5.5.
   (4) Infrared absorption spectrum (pelleted in KBr): With characteristic absorption peaks at 3500~3300, 1660 and 1550 cm$^{-1}$.

(5) Ultraviolet absorption spectrum in an aqueous solution: With a characteristic absorption peak $\lambda_{max}$ H$_2$O at 255 nm.

(6) Color reactions: Positive in biuret reaction, xanthoproteic reaction, phenolic reagent reaction according to Lowry-Folin method, anthrone-sulfuric acid reaction, phenol-sulfuric acid reaction and cysteine-sulfuric acid reaction.

(7) Average molecular weight: About 470,000 as measured by gel-electrophoresis.

2. A glycoprotein substance possessing an antitumor activity which is recovered from the liquid portion coming from cooking of raw scallop with a hot aqueous solvent or with the vapor of such solvent by concentrating the liquid portion to a smaller volume or to dryness to give a concentrate or dry powder, dissolving the concentrate or dry powder in water or an aqueous solvent to form an aqueous solution thereof and subjecting the aqueous solution to a series of treatments comprising ion-exchange chromatography with a basic anion exchanger and molecular weight-fractionating treatments comprising gel-filtration and electrophoresis, in any desired sequence, and which has the following characteristics:-

(1) Appearance: White, powdery solid.
(2) Solubility: Soluble easily in water, but insoluble in organic solvents such as methanol, ethanol and acetone.
(3) Acidic or basic nature: Amphoteric electrolyte having an isoelectric point of pH 5.5.
(4) Infrared absorption spectrum (pelleted in KBr): With characteristic absorption peaks at 3500~3300, 1660 and 1550 cm$^{-1}$.
(5) Ultraviolet absorption spectrum in an aqueous solution: With a characteristic absorption peak $\lambda_{max}$ H$_2$O at 255 nm.
(6) Color reactions: Positive in biuret reaction, xanthoproteic reaction, phenolic reagent reaction according to Lowry-Folin method, anthrone-sulfuric acid reaction, phenol-sulfuric acid reaction and cysteinesulfuric acid reaction.
(7) Average molecular weight: About 470,000 as measured by gel-electrophoresis.

3. A glycoprotein substance according to claim 2 wherein the treatments of the aqueous solution for the isolation of the desired glycoprotein substance therefrom are carried out in a buffer solution having a strong buffering action.

4. A process for the preparation of a water-soluble, antitumor glycoprotein substance having an average molecular weight of about 470,000 and an isoelectric point of pH 5.5 from scallop which comprises recovering the liquid portion which comes from cooking of raw scallop with a hot aqueous solvent or with vapor of such solvent and which is to be discarded as waste, concentrating the liquid portion thus recovered to a smaller volume or to dryness to yield a concentrate or dry powder, dissolving the concentrate or dry powder in water or an aqueous solvent to form an aqueous solution thereof and subjecting the aqueous solution to a series of treatments comprising ion exchange chromatography with a basic anion exchanger and molecular weight-fractionating treatments comprising gel-filtration and electrophoresis, in any desired sequence, whereby isolating a fraction consisting essentially of a glycoprotein substance which is adsorbable on a basic anion exchanger and which has an average molecular weight of about 470,000 and an isoelectric point of pH 5.5.

5. A process according to claim 4 wherein after the concentrate or dry powder is dissolved in water, the aqueous solution so formed is subjected to ion-exchange chromatography with a basic anion exchanger to recover a fraction adsorbed on the basic anion exchanger, and the fraction is then subjected to molecular weight-fractionating treatments comprising gel filtration and electrophoresis to isolate a fraction consisting essentially of a glycoprotein substance having an average molecular weight of about 470,000 and an isoelectric point of pH 5.5.

6. A process according to claim 4 wherein the treatments of the aqueous solution for the isolation of the desired glycoprotein substance therefrom are carried out in a buffer solution having a strong buffering action.

* * * * *